United States Patent [19]

Kimura et al.

[11] Patent Number: 5,751,418
[45] Date of Patent: May 12, 1998

[54] SPECTROMETRY AND OPTICAL METHOD AND APPARATUS FOR OBTAINING A STABLE SPECTRUM WITH USE OF AN INFORMATIONLESS SPECTRUM CONTAINED THEREIN

[75] Inventors: Eiichi Kimura; Naoki Yanai; Motonobu Shiomi, all of Neyagawa; Emi Ashibe, Kyoto; Yutaka Yamasaki, Kyoto; Harumi Uenoyama, Kyoto, all of Japan

[73] Assignees: Kurashiki Boseki Kabushiki Kaisha, Okayama-ken; Kyoto Daiichi Kagaku Co., Ltd., Kyoto, both of Japan

[21] Appl. No.: 644,202

[22] Filed: May 10, 1996

[30] Foreign Application Priority Data

May 11, 1995 [JP] Japan ................................ 7-113020

[51] Int. Cl.$^6$ ................................................ G01N 21/00
[52] U.S. Cl. ................. 356/319; 250/339.07; 250/339.09
[58] Field of Search .......................... 356/319, 323, 356/325, 326, 328, 418, 419; 250/339.07, 339.08, 339.09, 339.11, 339.12, 339.13

[56] References Cited

U.S. PATENT DOCUMENTS 4,097,743  6/1978  Carlson .
5,121,337  6/1992  Brown .

FOREIGN PATENT DOCUMENTS

0437249A2  7/1991  European Pat. Off. .
61-83922   4/1986  Japan ................................ 356/326

*Primary Examiner*—F. L. Evans

[57] ABSTRACT

In an optical measuring apparatus of the present invention, a spectroscopic optical system emits a measuring light beam that contains a measure light component of a measure wavelength domain where a measured object absorbs part of the light and a reference light component of a reference wavelength domain where the measured object almost completely absorbs the light, and separates the beam into beams, a photometric unit measures the light incident on an integrating sphere when a reference sample is inserted in the light path and stores the measurements in a memory and also measures the light incident on an integrating sphere when a measured object is inserted in the light path, and an arithmetic circuit calculates a light intensity ratio of the compensation light component for the measured object to the compensation light component stored in memory and then estimates background intensities during the measurement by multiplying the measurements stored in the memory by the intensity ratio.

20 Claims, 10 Drawing Sheets

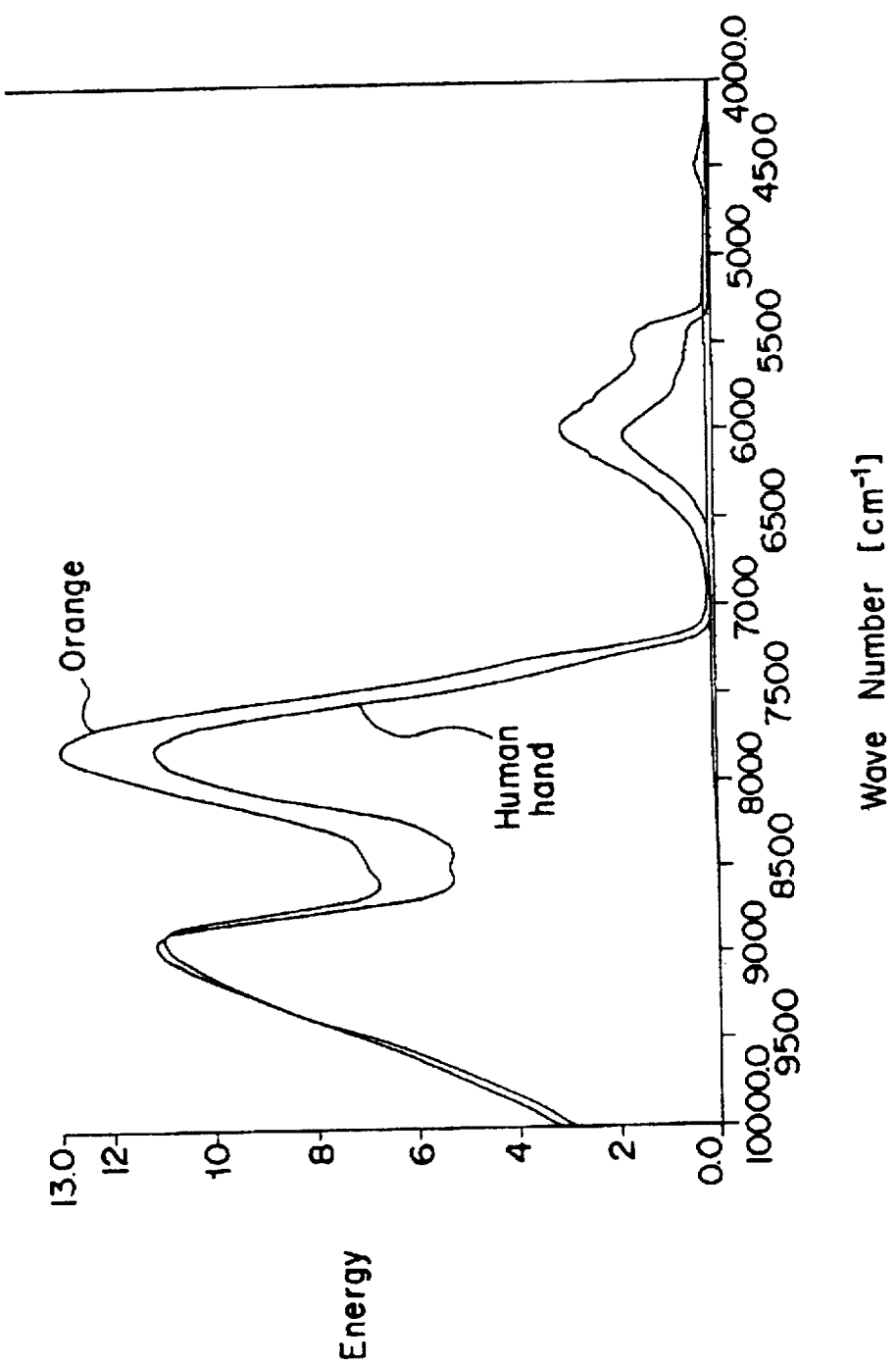

SPECTROMETRY AND OPTICAL METHOD AND APPARATUS FOR OBTAINING A STABLE SPECTRUM WITH USE OF AN INFORMATIONLESS SPECTRUM CONTAINED THEREIN

BACKGROUND OF THE INVENTION

1. Field of the Invention

The present invention relates to a spectrometry and optical method and apparatus for measuring material values such as component ratios, concentration, and thickness of an object by irradiating the object with light and measuring the spectrum of the light transmitted through or reflected by the object.

2. Description of the Related Art

In general, spectrometry is a well-known method of performing qualitative and quantitative analysis of an object for thickness, component concentrations, percentage of water content, and the like. The method usually irradiates light on the object and measures the spectrum of the light transmitted through or reflected by the object to detect the degree of the light absorbed by the object at a characteristic absorption wavelength.

In a prior optical measuring apparatus that performs such a measurement, drift occurs caused by the deterioration of the light source and changes in temperature due to changes in ambient temperature, the heating of the apparatus itself, and the like. Consequently, the quantity of reference light fluctuates. In order to solve this problem, prior techniques have measured the light quantity radiated from the light source to correct the quantity of reference light. These generally known prior apparatus are classified as follows:

(1) The operator temporarily removes the measured object from the measuring optical system to perform a reference measurement.

(2) The operator temporarily moves the measuring apparatus to a location separate from the measured object to perform the reference measurement.

(3) The light path of the optical system in the apparatus is divided into two branches, and the operator performs reference measurement by switching the light paths in a time sharing.

(4) The light path of the optical system in the apparatus is divided into two branches, and the operator performs the reference measurement by using one of the two detectors.

For example, an apparatus of the above construction (3) is disclosed in U.S. Pat. No. 4,097,743. That apparatus aims to improve the stability of the apparatus by monitoring the intensity of a light beam from the source not projected onto the measured object to eliminate the drift of the apparatus. However, since the above constructions (3) or (4) are complex, these apparatus are rarely adopted for industrial use.

An apparatus of the above construction (1), where reference measurement is performed by removing the measured object from the measuring optical system, requires a mechanism that removes the object. Consequently, the peripheral equipment becomes large, continual measurement is impossible, and frequent reference measurement is necessary. An apparatus of the above construction (2), where the apparatus itself is moved to a location separate from the measured object, requires a mechanism for moving the apparatus. Consequently, the peripheral equipment becomes large, continual measurement is impossible, and frequent relocation of the apparatus is necessary. Further, an apparatus of the above construction (3), where the light path of the optical system in the apparatus is divided into two branches, and the operator performs the reference measurement by switching the light paths in a time sharing manner, requires a mechanism for switching the light paths. Consequently, the apparatus itself becomes complex and large, and the frequency of malfunctions becomes high. Moreover, completely continual measurement is impossible, and the reference measurement and the sample measurement cannot be performed at the same time, since the light paths are switched in a time-sharing manner. Consequently, the drift of the apparatus cannot be eliminated. An apparatus of the above construction (4), where the light path of the optical system in the apparatus is divided into two branches, and the operator performs reference measurement by using one of two detectors, allows continual measurement, but there exists a difference between the two detectors. Consequently, adjustment of the two optical subsystems is difficult.

Another problem common to all the constructions (1) through (4) is that they generate large errors, when the spectra of light having no information concerning the measured object absorbance (herein after referred to as "spectra") are contained in the absorption spectrum. Such informationless light concerning the measured object is, for example, stray light occurring during the measurement of transmittance, leaking light due to an insufficient size of the sample, and specular reflection light reflected by the surface varying with the surface state and the grain size of the sample during the measurement of reflectance.

SUMMARY OF THE INVENTION

An object of the present invention is to provide an optical measuring method that eliminates informationless spectra concerning the measured object to reduce the errors in spectroscopic measurements.

Another object of the present invention is to provide an optical measuring method that obtains accurate information about the light transmitted through or reflected by the measured object without being affected by informationless spectra, differences in characteristics of individual photo detectors, or drift.

Another object of the present invention is to provide an optical measuring apparatus that obtains accurate information about the light transmitted through or reflected by the measured object without being affected by informationless spectra, differences in characteristics of individual photo detectors, and drift.

The present invention is based on the following consideration. In general, spectroscopic measurement is performed in a dark place where no intervention light exists. However, it is hard to eliminate intervention light for some shapes of measured objects. Further, in the measurement of reflectance, methods of separating and detecting intervention light and methods of normalizing at neutral wavelengths where no absorption occurs are employed. An example of the former methods is the 45°-detecting technique. Examples of the latter methods are single-wavelength compensation, double-wavelength compensation, and differential spectral compensation. However, these methods cannot eliminate intervention light and have the possibility of distorting data in compensation.

If a sample of the measured object absorbs a large amount of light at a particular wavelength, and if the size of the sample is sufficiently large so that the transmitted or reflected light is hardly detected at that wavelength under the condition of non-existence of intervention light, then a spectrum containing intervention light is totally due to intervention light. Intervention light is informationless light concerning the sample and produces a certain ratio of the spectrum of the light source. Therefore, the informationless spectrum of intervention light can be obtained by multiplying the spectrum of the light source by a coefficient so that the result agrees with the measured spectrum at that particular wavelength. The real spectrum of transmitted or reflected light is obtained by subtracting the spectrum of the intervention light from the measured spectrum. The real spectrum of incident light is also obtained by subtracting the spectrum of intervention light from the spectrum of the light source.

On the other hand, there is a demand to measure component concentrations such as percentage of oxygen saturation in blood, percentage of fat in the body and the like. The main component of the human body is water, about 60 to 70%, and a long light path is required in measuring reflected light as well as transmitted light, since the body is a scatterer. Therefore, as seen from an absorption spectrum shown in FIG. 11, no light is transmitted at the characteristic absorption wavelengths for O-H i.e., 1.4 μm and those longer than 1.9 μm. FIG. 11 also shows an absorption spectrum of an orange. In the case of measuring the sugar concentration or ripeness of fruits such as oranges, apples, and peaches, no light is transmitted at the characteristic absorption wavelengths for O-H, i.e., 1.4 μm and those longer than 1.9 μm. Similarly, no light is transmitted at the characteristic absorption wavelengths for C-H. Therefore, as described in the following, the present invention uses the characteristic absorption wavelengths, where the light is almost completely absorbed, for compensation together with their side bands to measure absorption spectra.

According to the present invention, the whole beam of the light source is divided into a measure optical system and a reference optical system at a certain ratio. First, the reference beam is measured, and the signal intensities at the above wavelengths for compensation and at wavelengths for measurement are stored (Registration of reference light). In the state such that the measured object is arranged in the measure optical system, if the total beam of the measure optical system and the reference optical system is measured, then the light transmitted through or reflected by the measured object is not detected at all at a wavelength for compensation, so that the measured result shows the light quantity of the reference optical system. Now, consider the ratio of this light intensity to the stored signal intensity at the same wavelength for the reference optical system only or for a reference sample. If we multiply the stored signal intensity at every wavelength by that ratio, then we can estimate the light quantity during actual measurement at each wavelength.

From the relationship,

Measured light quantity =

Light quantity of measure optical system + light quantity of reference optical system, the following equation (1) is obtained for the registration of reference light at time $t_0$.

$$I_m = \beta I_0, \quad (1)$$

where $I_0$ is the total light quantity, $I_m$ is the measured light quantity, and $\beta$ is the ratio of the light quantity of the reference optical system to the total light quantity.

Further, the following equations (2) and (3) hold for the measurement of absorbances at time $t_1$ and $t_2$.

$$I_m' = \alpha_1 I_0' + \beta I_0', \quad (2)$$

$$I_m'' = \alpha_2 I_0'' + \beta I_0'', \quad (3)$$

Here $I_0'$, $I_0''$ are the total quantities of light respectively at time $t_1$, $t_2$, and $I_m$, $I_m'$ are the intensities of measured light respectively at time $t_1$ and $t_2$. Also, $\alpha_1$, $\alpha_2$ are the transmission or reflection coefficients that depend on wavelengths, and the ratio 0 of the light quantity of the reference optical system to the total light quantity is independent of wavelengths.

If the wavelength $\lambda$ is equal to the wavelength C for compensation, then $\alpha_2 = \alpha_2 = 0$, so that the following equations (4) and (6) are obtained from (1) through (3).

$$I_{m\lambda=C} = \beta I_{0\lambda=C}, \quad (4)$$

$$I_{m\lambda=C}' = \beta I_{0\lambda=C}', \quad (5)$$

$$I_{m\lambda=C}'' = \beta I_{0\lambda=C}''. \quad (6)$$

From the equations (4) and (5) the following equation (7) is obtained. Similarly, (8) is obtained from (4) and (6):

$$I_{m\lambda=C}'/I_{m\lambda=C} = I_{0\lambda=C}'/I_{0\lambda=C}, \quad (7)$$

$$I_{m\lambda=C}''/I_{m\lambda=C} = I_{0\lambda=C}''/I_{0\lambda=C}. \quad (8)$$

Now, set the above equations (7) and (8) respectively as $$I_{m\lambda=C}'/I_{m\lambda=C} = I_{0\lambda=C}'/I_{0\lambda=C} = n', \quad (9)$$

$$I_{m\lambda=C}''/I_{m\lambda=C} = I_{0\lambda=C}''/I_{0\lambda=C} = n''. \quad (10)$$

Since $I_0'/I_0$ and $I_0''/I_0$ in the equations (9) and (10) have no dependence on wavelengths, the following equations (11) and (12) are obtained by extending them to the whole wavelength domain.

$$I_0'/I_0 = n' (= I_{m\lambda=c}'/I_{m\lambda=c}), \quad (11)$$

$$I_0''/I_0 = n'' (= I_{m\lambda=c}''/I_{m\lambda=c}). \quad (12)$$

Then the following equations (13) and (14) follow from the equations (11) and (12).

$$I_0' = n' \times I_0 = n' I_m/\beta, \quad (13)$$

$$I_0'' = n'' \times I_0 = n'' I_m/\beta. \quad (14)$$

The absorbances are obtained from the equations (13), (14), (2), and (3) as in the following equations (15) and (16).

$$abs' = -\log(\alpha_1) \quad (15)$$
$$= -\log\{(I_m' - n' I_m)/n' I_m\} - \log\beta,$$

$$abs'' = -\log(\alpha_2) \quad (15)$$
$$= -\log\{(I_m'' - n'' I_m)/n'' I_m\} - \log\beta.$$

Here, $-\log \beta$ is a constant term, and can be contained in the analytical curve, so that it can be neglected in the operations of quantitative analysis. However, $\beta$ can be obtained in the following way, if necessary. That is, in the reference measurement, no measured object is arranged in the case of transmission, and a standard sample is arranged in the case of absorption. Then light intensities are measured by switching the light paths between the measure path and the reference path. Then $\beta$ is obtained as the ratio of the obtained measurements.

Since the measurements for absorbances are the sums of the light quantities of the measure optical system and the reference optical system, the light quantities of the measure optical system are obtained by subtracting the estimated light quantity of the reference optical system from the measurements. Further, the light quantity of the reference optical system is in a constant ratio of the total light quantity, that is, in proportion to the total light quantity, so that the two can be regarded as the same in quantitative analysis. Still, the ratio can be measured, so that the total light quantity can be monitored, and drift can be eliminated.

The present invention is based on the above consideration. The present invention is directed to an optical measuring method that irradiates a measured object with light from a light source and measures the spectrum of the light transmitted through or reflected by the measured object. The light source generates measuring light of wavelengths including those on a compensation wavelength domain where the measured object almost completely absorbs the light. The method first measures the spectrum of the light generated by the light source, and next irradiates the measured object from the light source to measure the spectrum of the light transmitted through or reflected by the measured object. Then, the method calculates the ratio of the intensity of the transmitted or reflected light to the intensity of the light generated by the source at a compensation wavelength, and multiplies the intensity of the light generated by the source at each wavelength by that ratio to obtain an informationless spectrum. Finally, the method obtains a compensated measure spectrum by subtracting the informationless spectrum from the measured spectrum of the transmitted or reflected light.

In one embodiment of the optical measuring method according to the present invention, the difference spectrum between the spectrum of the light generated by the source and the informationless spectrum as the compensated source spectrum of the light incident on the measured object. Then, the method obtains the absorbance spectrum from the compensated measure spectrum and the background spectrum that is the compensated source spectrum. Finally, the method measures a material value of the measured object based on the absorbance spectrum.

Further, another embodiment of the present invention obtains a temporary absorbance spectrum from the compensated measure spectrum and the background spectrum that is the spectrum of the light generated by the source. Then, the method compensates the temporal absorbance spectrum for its additive errors by baseline compensation or differentiation to obtain an absorbance spectrum. Finally, the method measures a material value of the measured object based on the absorbance spectrum.

Still further, another embodiment according to the present invention measures the absorbance spectrum by adding a reference material to the measured object so that the absorbances in the compensation wavelength domain become zero.

Further, another embodiment according to the present invention is characterized in that the reference material is water.

Further, another embodiment according to the present invention is characterized in that the compensation wavelength domain is the absorption wavelength domain for O-H in the optical measuring method according to the present invention.

Further, still another embodiment according to the present invention is characterized in that the compensation wavelength domain is the absorption wavelength domain for C-H in the optical measuring method according to the present invention.

Further, a further embodiment according to the present invention is an optical measuring apparatus that irradiates a measured object with light to measure the intensities of the light transmitted through or reflected by the measured object and measures a material value owned by the measured object based on the measurements. The apparatus comprises the following components:

a light source that generates measuring light of a measure wavelength domain for measuring a material value owned by the measured object and of a compensation wavelength domain where the light is almost completely absorbed by the measured object;

a spectroscopic optical system means that splits the measuring light into the measure wavelength domain and the compensation wavelength domain;

a light path optical system means that directs the measuring light emitted from the light source to a first branch light path and a second branch light path, arranges the measured object in the second branch light path, and rejoins the light from the first branch and second branch paths;

a photometric means that measures the light emitted from the light path optical system means to detect the intensities of the light split into the measure wavelength domain and the compensation wavelength domain;

a memory means that stores the light intensities of the measure wavelength domain and the compensation wavelength domain output from the photometric means during a reference measurement when a light-blocking material is arranged in or the measured object is removed from the second branch light path; and an arithmetic means that calculates the ratio of a light intensity on the compensation wavelength domain detected by the photometric means during ordinary measurement when the measured object is arranged in the second branch light path to a light intensity on the compensation wavelength domain stored in the memory means, obtains absorbances by arithmetically processing the light intensity ratio, the light intensities stored in the memory means, and the output of the photometric means during the ordinary measurement, and determines the material value of the measured object based on the absorbances.

Still further, another according to the present invention is characterized in that in the optical measuring apparatus, the arithmetic means performs the computation $-\log\{(I_m = n \times I_o)/(n \times I_o)\}$ for the light intensities $I_o$ stored in the memory means and the output values $I_m$ of the photometric means during the ordinary measurement, where n is the light intensity ratio.

Further, one more embodiment according to the optical measurement apparatus of the present invention is characterized in that the light path optical system means includes an optical fiber, which has a first branch section that forms the first branch optical path and a second branch section that forms the second branch optical path, and the second branch section has in its path a measuring part where the measured object is arranged.

Further, another embodiment of the present apparatus according to the present invention is characterized in that the light path optical system means has an integrating sphere, on which the photometric means is arranged.

Still further, another embodiment according to the present apparatus of the present invention is characterized in that the light path optical system means comprises an integrating sphere and a light cone that is arranged inside the integrating sphere and has an optical opening that opens inside the integrating sphere.

Still further, another embodiment according to the present apparatus of the present invention is characterized, the spectroscopic optical system means is an interference optical system of the Fourier transform type.

Still further, another embodiment of the present apparatus according to the present invention is characterized in that the spectroscopic optical system means has a rotating disk that is equipped with a filter that transmits the light of the measure wavelength domain and the compensation light of the compensation wavelength domain that is almost completely absorbed by the measured object.

Still further, another embodiment of the invention apparatus according to the present invention is characterized in that the spectroscopic optical system means is a monochromator of the diffraction grating type.

Still further, another embodiment of the optical measuring apparatus according to the present invention is characterized in that the spectroscopic optical system means is a monochromator of the prism type.

The light of the compensation wavelength domain incident on the measured object is almost completely absorbed by the measured object. Therefore, the spectrum of informationless intervention light can be obtained by calculating the ratio of the light intensity from the measured object to the light intensity from the light source in the compensation wavelength domain and by multiplying the spectrum of the light source by the intensity ratio.

The difference spectrum between the spectrum of the light source and the spectrum of the informationless intervention light becomes the compensated spectrum of the light source incident on the measured object. Therefore, the absorbance spectrum is obtained from the background spectrum that is the compensated spectrum of the light source.

Further, if the measured object does not have a compensation wavelength domain, then the informationless intervention light component can be eliminated in the above method by adding a reference material that has a wavelength domain where the light is almost completely absorbed.

If the measured object contains sufficient water, the absorption wavelength domain for water can be used as the compensation wavelength domain to eliminate the informationless intervention light component from the measured spectrum by the above method.

The arithmetic means calculates the light intensity ratio of the measurement of the joined compensation light from the first branch light path and the second branch light path to the measurement of the compensation light stored in the memory means. The joined compensation light is measured, when the measured object is arranged in the second branch light path. The arithmetic means obtains a material value of the measured object by arithmetically processing the light intensity ratio, the measurements stored in the memory means, and the measurements of the joined light from the first branch light path and second branch light path. In particular, the arithmetic means calculates $-\log\{(I_m-n\times I_o)/(n\times I_0)\}$.

The photometric means measures the light of the first branch and second branch light paths combined by the integrating sphere.

The interference optical system of the Fourier transform type splits the light from the source into the measure light component and the compensation light component. The rotating disk also splits the light from the source into the measure light component and the compensation light component.

The optical fiber divides the light from the source into the first branch section and the second branch section, and the measured object is arranged in the measuring part of the second branch section.

The monochromator of the diffraction grating type splits the light from the source into the measure light component and the compensation light component. The monochromator of the prism type also splits the light from the source into the measure light component and the compensation light component.

The light directly emitted from the optical opening of the light cone and the light reflected by the measured object are made incident on the integrating sphere.

The informationless light has the same information as the spectrum of the light source, and therefore has a geometrically similar spectrum. According to the present invention, the spectrum component of the informationless light can be obtained by multiplying the spectrum of the light source by the intensity ratio of the light from the measured object to the spectrum of the light source in the compensation wavelength domain. Therefore, the informationless light component can be removed from the measured spectrum by subtracting the spectrum of the informationless light from the measured spectrum.

Further, according to the present invention, the spectrum of the informationless light becomes a compensation spectrum proportionate to the spectrum of the light source. Therefore, a material value owned by the measured object can be obtained from the absorbance spectrum that is calculated from the background spectrum that is the compensation spectrum.

Further, the present invention calculates the ratio of the measurement of the joined compensation light of the first branch and second branch light paths, when the measured object is arranged in the second branch light path. A material value of the measured object is determined by arithmetically processing the light intensity ratio, the measurements stored in the memory means, and the measurements of the joined compensation light of the first branch and second branch light paths obtained when the measured object is arranged in the second branch light path. Consequently, the measurement of the compensation light stored in the memory means has to be obtained only once after the construction of the apparatus and after the replacement of parts that depend on wavelength, such as the light source, the photometer, and the like. In this way, the drift of the apparatus can be continually compensated, so that continual measurement of the measured object becomes possible.

Still further, according to the present invention, drift can be continually removed from the measurements of a material value of the measured object by the arithmetic operation $-\log\{(I_m-n\times I_o)/(n\times I_0)\}$.

Still further, according to the present invention, the light of the first branch and the second branch light path can be combined by an integrating sphere and measured by a photometer.

Further, according to the present invention, light can be split into a measure light component and a compensation light component with high precision by an interference optical system of the Fourier transform type.

Further, according to the present invention, light can be split into a measure light component and a compensation component with comparatively simple constructions and at low costs by a rotating disk.

Further, according to the present invention, first branch and second branch light paths can be easily constructed by an optical fiber. Moreover, since an optical fiber can be easily bent, the arrangement of the first branch and second branch light paths in the apparatus can be flexible.

Further, light can be split into the measure light and the compensation light with high precision by a monochromator of the dispersion type.

Further, according to the present invention, light can be split into the measure light and the compensation light with high precision by a monochromator of the prism type.

Further, according to the present invention, the light directly emitted from the optical opening of the light cone and the light reflected by the measured object are made incident on the integrating sphere. Consequently, the first branch and second branch light paths become compact, so that the dimensions of the apparatus can be made small.

Further, according to the present invention, one detector is used throughout, so that compensation is simultaneous, no time delay occurs, and no sensitivity difference occurs. Moreover, accidents rarely occur, since the switching mechanism is fixed.

BRIEF DESCRIPTION OF THE DRAWINGS

These and other objects and features of the present invention will become clear from the following description taken in conjunction with the preferred embodiments thereof with reference to the accompanying drawings throughout which like parts are designated by like reference numerals, and in which:

FIG. 11 shows absorption spectra of an orange and a human hand.

DETAILED DESCRIPTION OF THE PREFERRED EMBODIMENTS

The preferred embodiments according to the present invention will be described below with reference to the appended drawings.

First Embodiment

Figure 1:
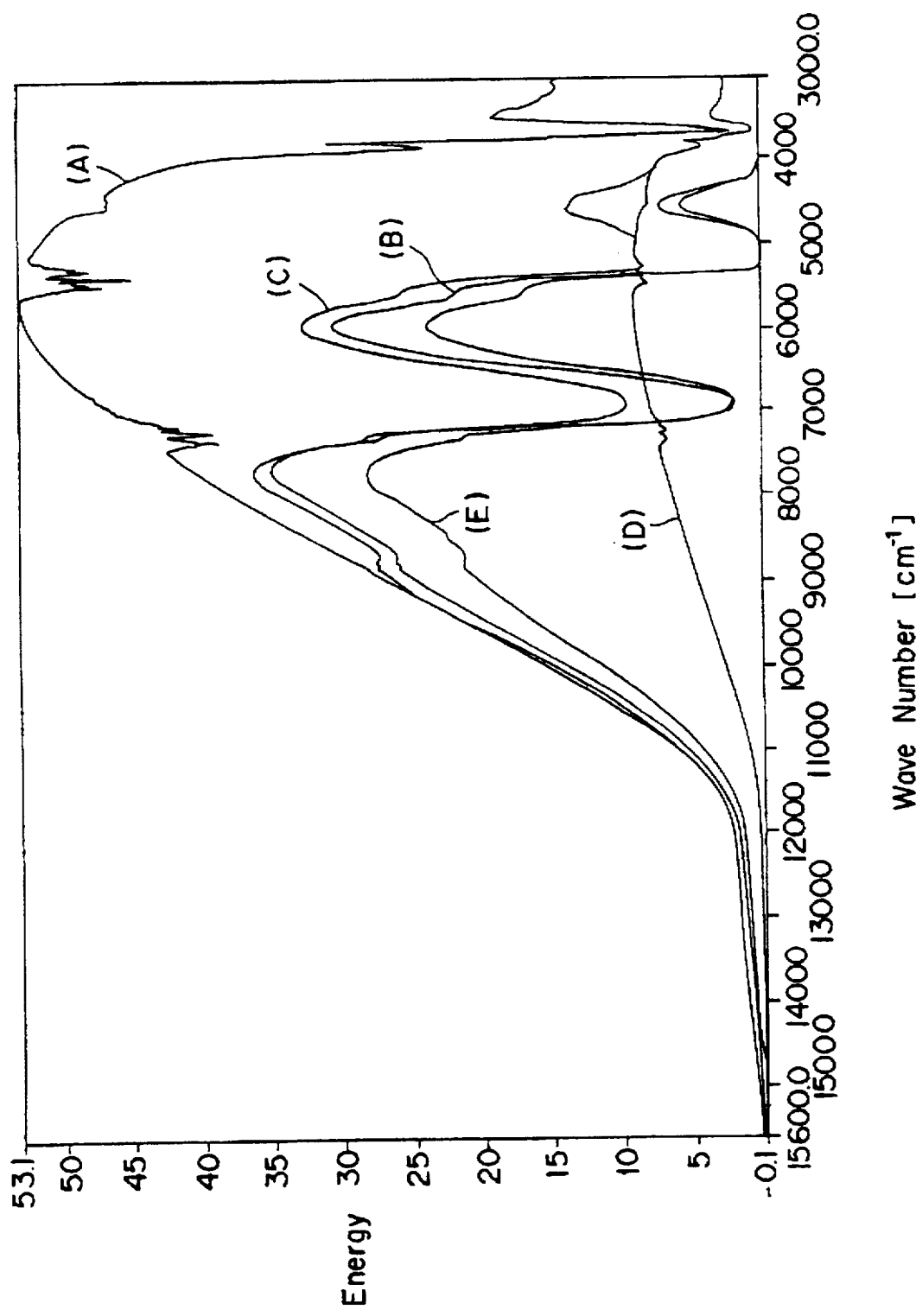
FIG. 1 shows near-infrared transmittance spectra of water obtained when the amount of water in a cell is varied.

FIG. 1 shows the results of measuring near-infrared transmittance spectra of water by varying the amount of water in a cell. In FIG. 1, the curve A shows the spectrum of the light source, the curve B shows the spectrum where the cell is filled with water, and the curve C shows the spectrum where the cell is partly filled with water. The absorption by water is particularly great at 5200 cm$^{-1}$, and the transmittance becomes almost zero. However, in the curve C, the transmitted light is detected at 5200 cm$^{-1}$. This transmitted light is the light not passing through the water but passing through only the cell, that is, it is the informationless intervention light that does not have any information about the absorbance by water. The spectrum of this intervention light has the same information as the spectrum of the light source, so that it has a geometrically similar shape as the curve A of the light source spectrum. Therefore, the spectrum D of the intervention light is obtained by multiplying the spectrum of the light source by a coefficient so that the result is equal to the energy value of the spectrum C at 5200 cm$^{-1}$. The difference obtained by subtracting the spectrum D from the spectrum C is the compensated measured spectrum E of the light that has passed through water. The difference obtained by subtracting D from A is the spectrum of the compensated spectrum of the light that has been incident on the sample.

Figure 2:
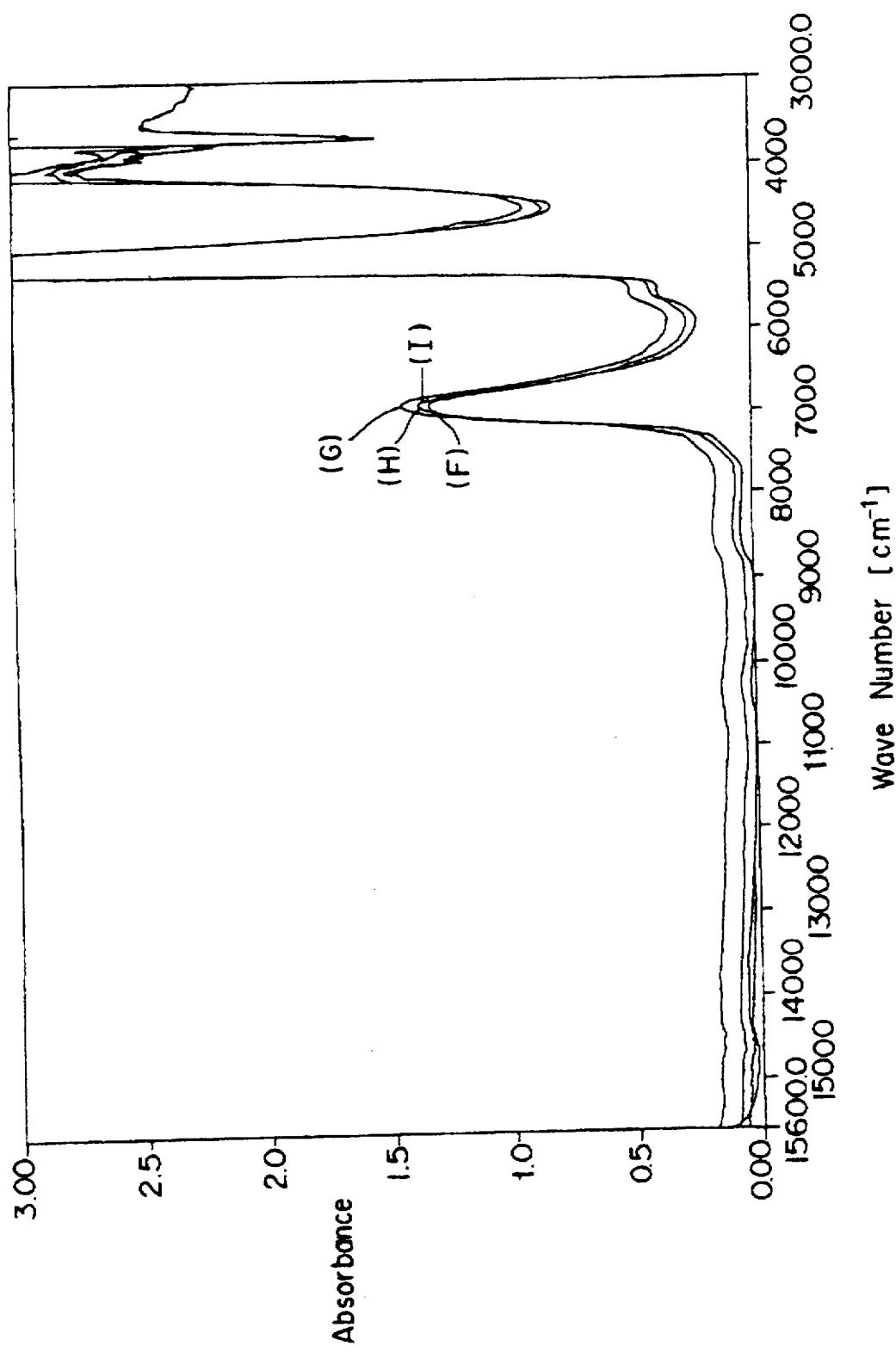
FIG. 2 shows absorbance spectra obtained after compensation.

FIG. 2 shows an absorbance spectrum F where the cell is filled with a sample material, the compensated measured absorption spectrum G where the light source spectrum is made the background spectrum, the compensated spectrum H obtained by baseline compensation from the compensated measured absorption spectrum G, and the compensated measured absorption spectrum I where the compensated light source spectrum is made to be the background spectrum.

Figure 3:
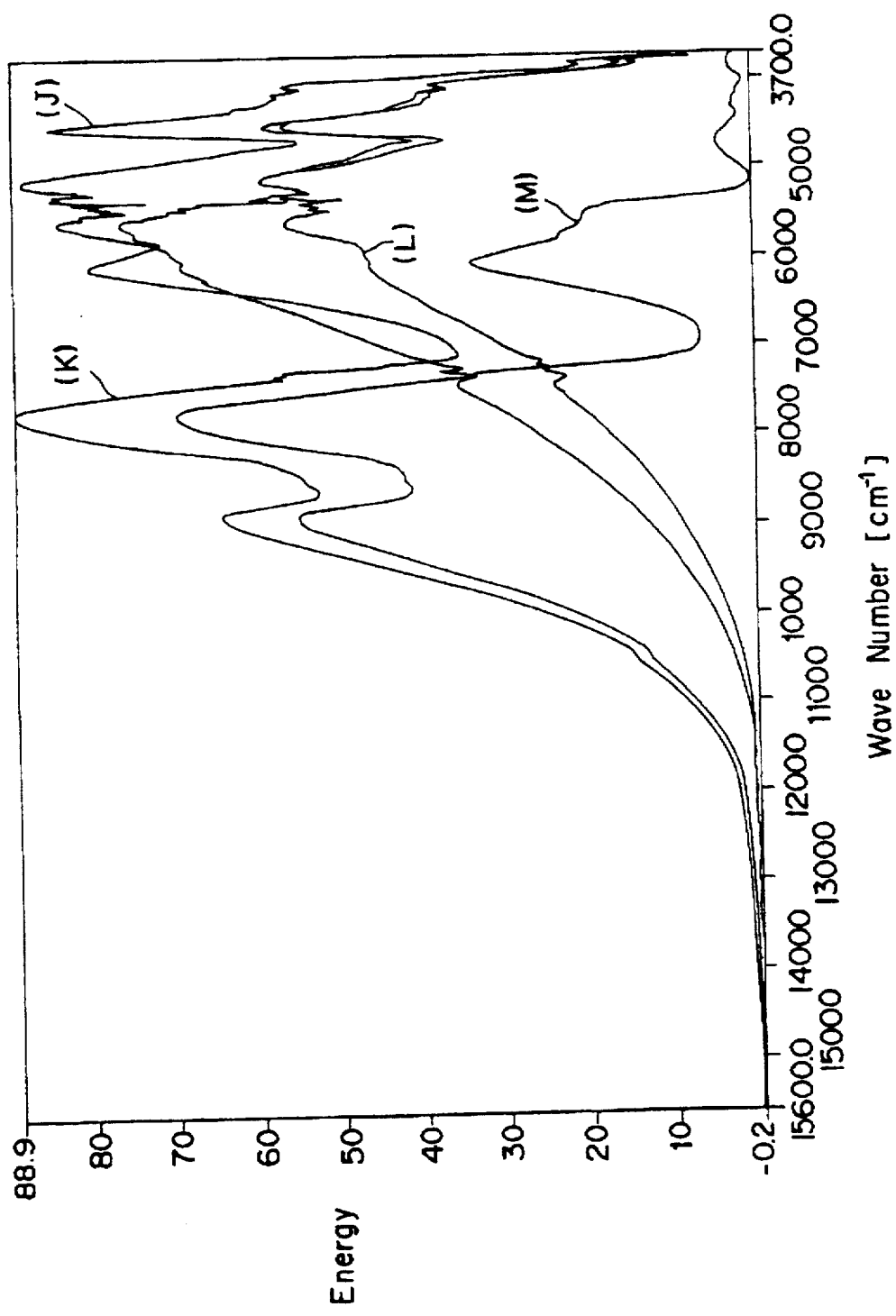
FIG. 3 shows near-infrared reflection energy spectra of human skin.

FIG. 3 shows a near-infrared diffuse reflectance energy spectrum of human skin. In FIG. 3, the curve J shows the light source spectrum, and K shows the sample spectrum. The absorption by water is particularly great at 5200 cm$^{-1}$, and the transmittance becomes approximately zero. Living organisms are full of water, but light is detected even at 5200 cm$^{-1}$. This light is the component that has not passed through the sample, that is, specular reflection light, which is intervention light that does not have information about the sample. This intervention light has the same information as the light generated by the source, so that it has a geometrically similar shape of spectrum as the light source spectrum J. Therefore, the spectrum L of the intervention light can be obtained by multiplying the light source spectrum J by a coefficient so that the resulting spectrum has the same energy value as the spectrum K at 5200 cm$^{-1}$. The difference obtained by subtracting the spectrum L from the spectrum K is the compensated measured spectrum M of the light that has been diffuse reflected by the sample. Consequently, in the compensated measured spectrum M, effects of the intervention spectrum L are absent. Also, the difference obtained by subtracting the intervention spectrum L from the light source spectrum J is the spectrum of the compensated spectrum of the light that has been incident on the sample.

Second Embodiment

Figure 4:
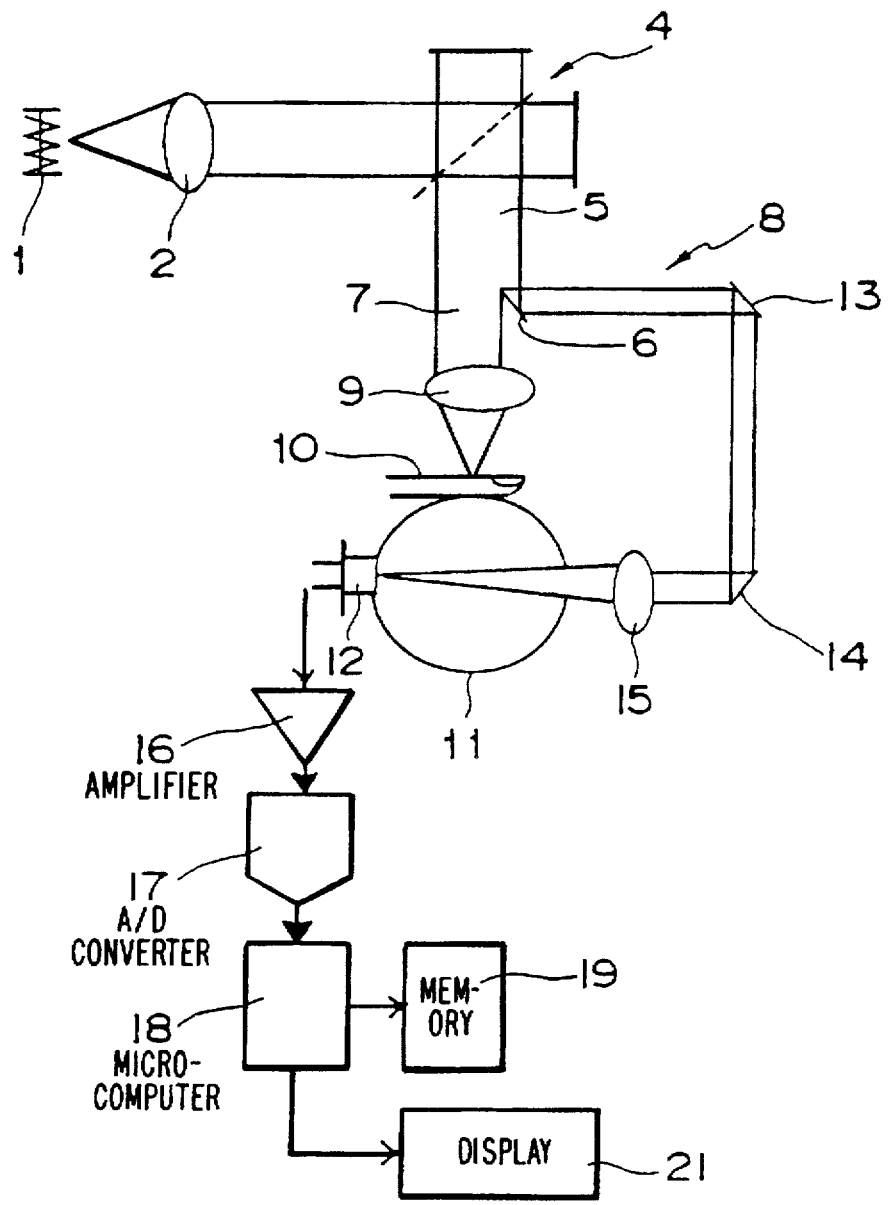
FIG. 4 shows a block diagram of an embodiment of optical measuring apparatus in accordance with the present invention.

FIG. 4 shows the construction of one embodiment of the optical measuring apparatus of the present invention. This apparatus measures components of human body fluids by irradiating a finger with infrared light. The apparatus comprises a nichrome lamp 1 that generates infrared light, a collimating lens 2 that converts the infrared light emitted from nichrome lamp 1 into a parallel beam, an interference optical system 4 of the Fourier transform type, and a mirror 6 that separates part of the beam 5 emitted from the interference optical system 4 of the Fourier type. A beam of infrared light is made incident from nichrome lamp 1 on the interference optical system 4 of the Fourier transform type, which splits the infrared light beam and emits a measuring light beam that contains a measure light component and a compensation light component. The measure light component has wavelengths of a measure wavelength domain where components of human body fluids absorb. The compensation light component has wavelengths of a compensation wavelength domain where the measured object almost completely absorbs the light. Mirror 6 separates the beam 5 emitted from interference optical system 4 of the Fourier transform type into beams 7 and 8.

The optical measuring apparatus further includes a lens 9 that concentrates the beam 7, an integrating sphere 11 on which the beam 7 is incident after passing through the measured object, i.e., a human finger 10, an infrared detector 12 of the PbS type, mirrors 13, 14 and a lens 15 that make the beam 8 detour the finger 10 and direct it the integrating sphere 11, an amplifier 16, an A/D converter 17, a microcomputer 18, memory 19 of microcomputer 18, and a display 21. The A/D converter 17 converts the signal output from infrared detector 12 of the PbS type and amplified by amplifier 16 into a digital signal to output into microcomputer 18.

The microcomputer 18 has two modes a reference signal measurement mode and an ordinary measurement mode. These reference signal measurement and ordinary measurement modes are switched by a mode switch, which is not shown in FIG. 4.

In the reference signal measurement mode, the opening of integrating sphere 11 is closed to block the measure beam 7, and only the reference beam 8 is measured by infrared detector 12 of the PbS type. The microcomputer 18 then stores, in memory 19, the measurements of the reference beam 8 converted into a digital signal by A/D converter 17. Alternatively, in the reference signal measurement mode, the opening of integrating sphere 11 may be kept open, and in place of the measurements of the reference beam 8 only, the output of the infrared detector 12 of the PbS type may be stored in memory 19 during the passing of the measure beam 7.

On the other hand, in the ordinary measurement mode, the measured object that is (a human finger 10) is placed at the opening of integrating sphere 11. In this state, the reference beam 8 and part of the measure beam 7 that has passed through the finger 10 are measured by the infrared detector 12 of the PbS type. The microcomputer 18 performs computations based on the equations (9) through (16) described already for these measurements and the stored measurements of the reference beam in memory 19. Specifically, the microcomputer 18 executes operations for equations (9) and (10), and calculates the light intensity ratio of the signal intensity measured by the Pbs infrared detector 12 at a compensation wavelength to the signal intensity at a compensation wavelength stored in memory 19. The microcomputer 18 also executes operations for equations (13) and (14) to estimate the background intensities during measurement by multiplying the signal intensities stored in memory 19 by the light intensity ratio n. Microcomputer 18 further executes operations for equations (15) and (16) to subtract the estimated background intensities from the measurements in the ordinary measurement mode. The microcomputer 18 then divides the results by the background intensities and calculates the logarithm of the inverse of the results to obtain absorbances. Based on the absorbances obtained in this way, the microcomputer 18 further performs multivariate analysis to calculate the component concentrations of human body fluids and present the results on display 21.

Figure 5:
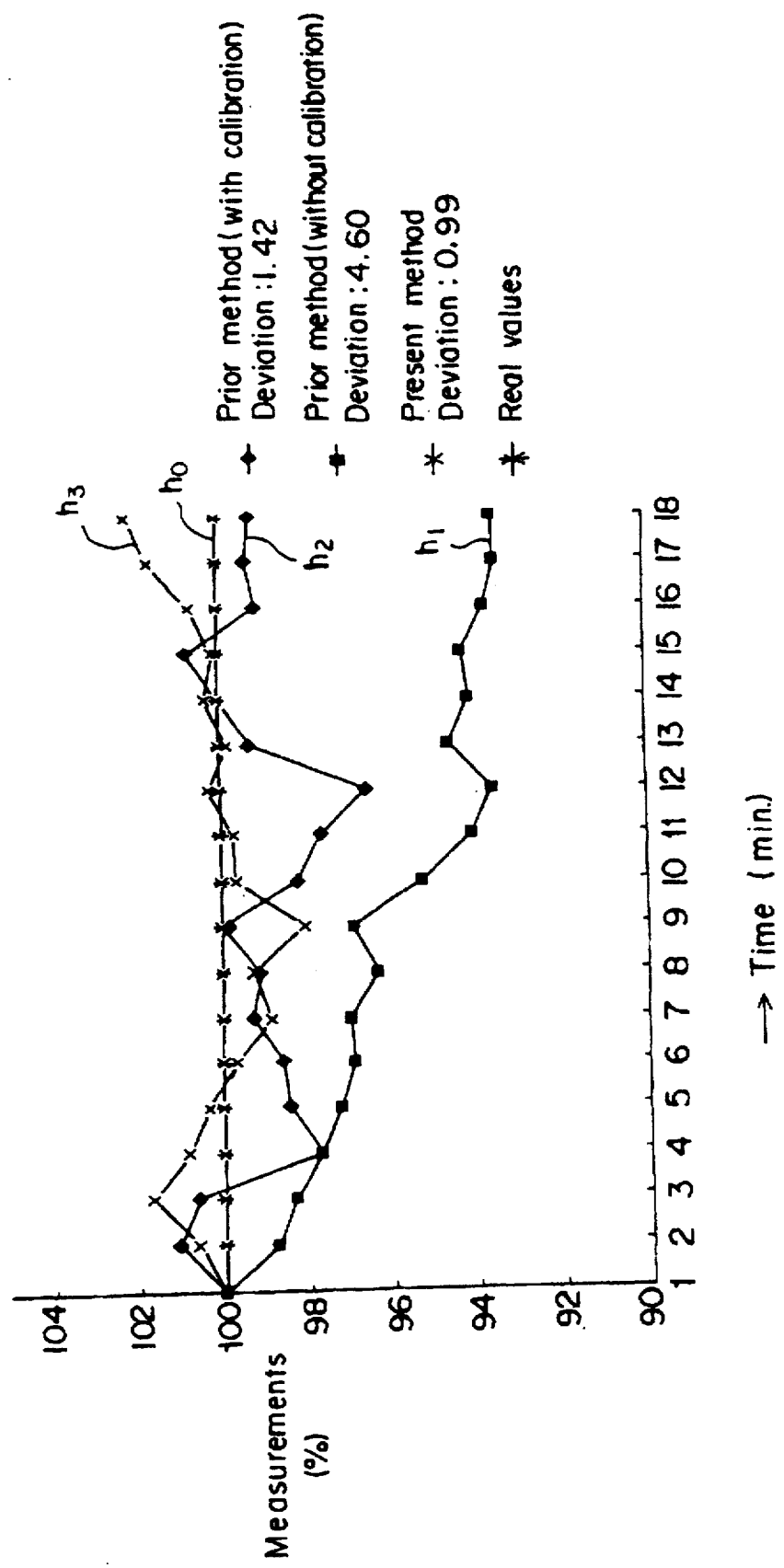
FIG. 5 shows graphs comparing the drift of the optical measuring apparatus of FIG. 4 with the drift of prior optical measuring apparatus.

Measurements obtained by the optical measuring apparatus of FIG. 4 described above are compared with measurements obtained by a prior apparatus in FIG. 5. In FIG. 5, the line $h_0$ shows real values, the broken line $h_1$ shows the drift of a prior apparatus using the so-called single-beam method, and the broken line $h_2$ shows the drift of a prior apparatus using the so-called double-beam method, which is disclosed in U.S. Pat. No. 4,097,743. The broken line $h_3$ shows the drift of the optical measuring apparatus of the present embodiment shown in FIG. 4. As shown in FIG. 5, all of these apparatuses are adjusted so that measurement starts one minute after they are activated, when their measurements agree with the real value 100%. The deviations shown in FIG. 5 are calculated with respect to the real values.

As seen from FIG. 5, the deviation of measurements by the optical measuring apparatus of the present embodiment is 0.99, while the deviation by the apparatus of the single-beam method is 4.60, and the deviation by the apparatus of the double-beam method is 1.42. Therefore, the drift of the apparatus of the present embodiment is greatly reduced.

Third Embodiment

Figure 6:
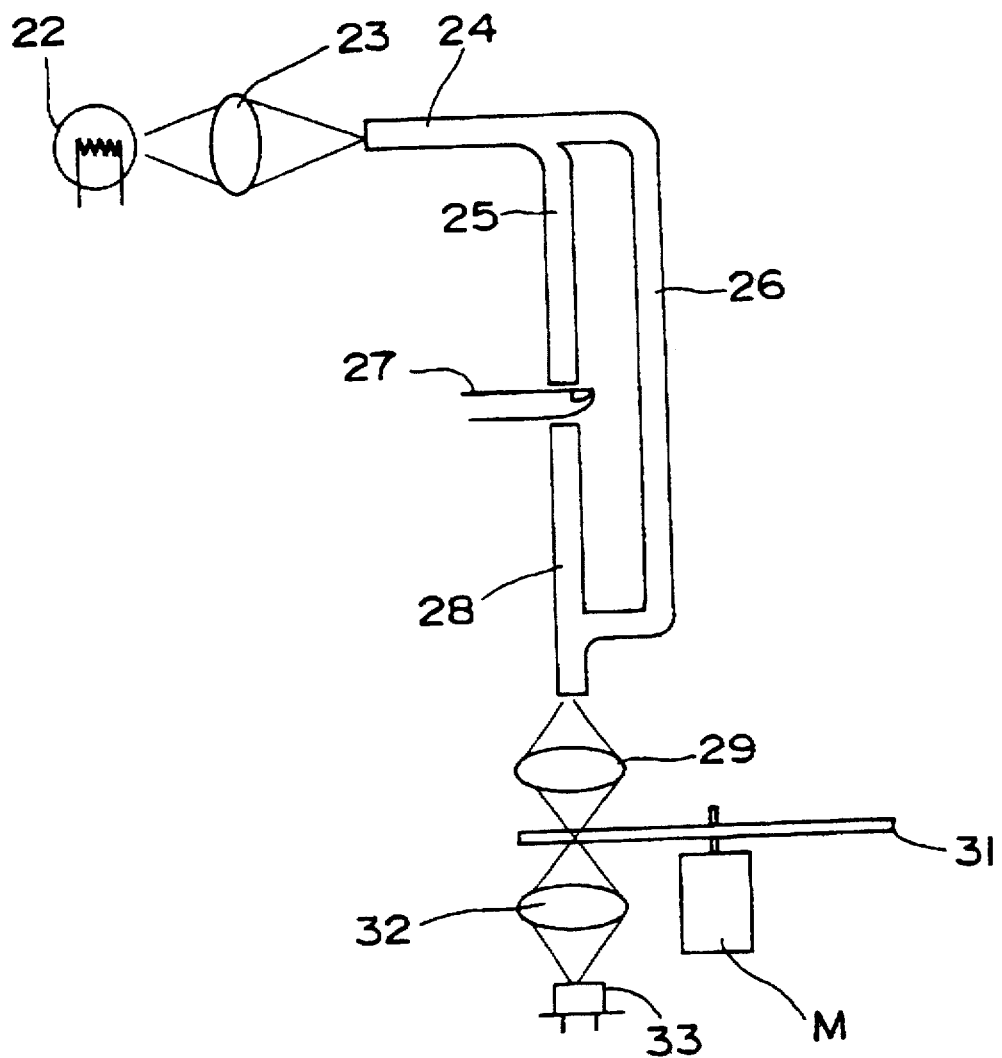
FIG. 6 shows a block diagram of another embodiment of optical measuring apparatus in accordance with the present invention.
Figure 7:
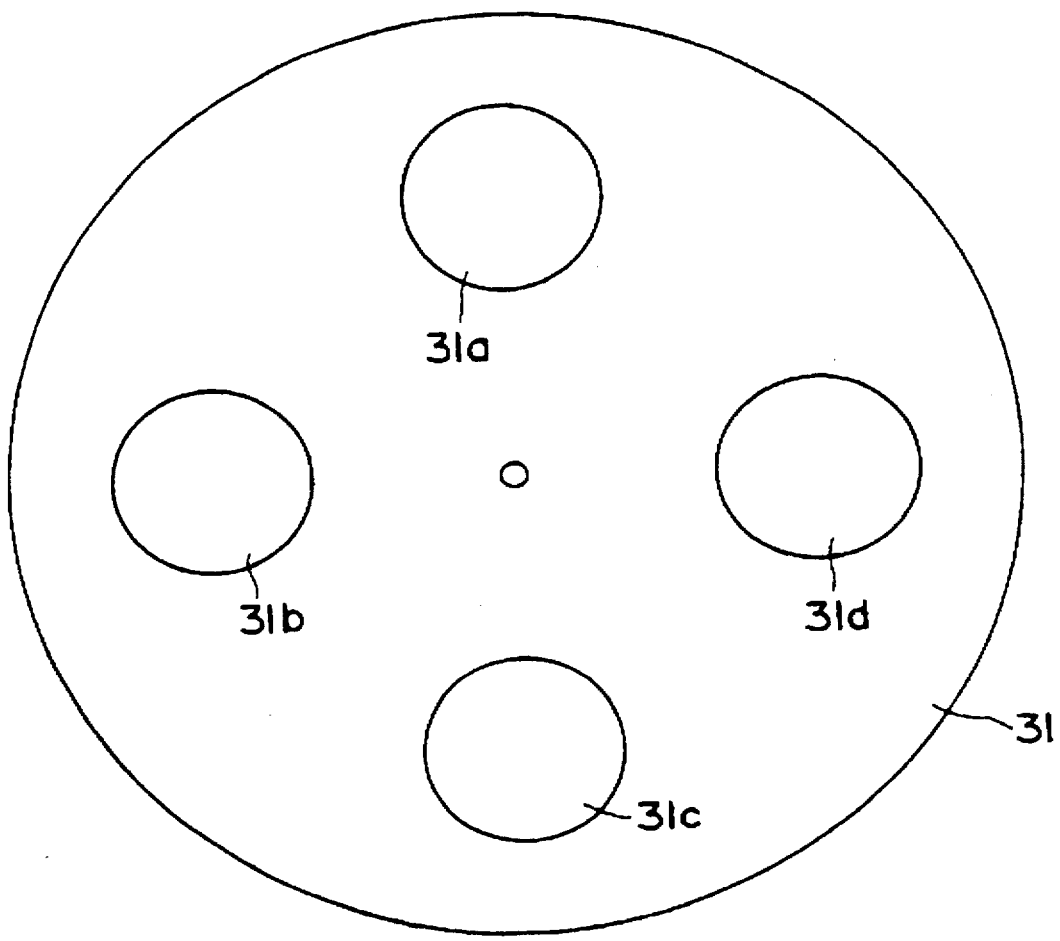
FIG. 7 shows a top view of a rotating disk used in the optical measuring apparatus of FIG. 6.

Fig. 6 shows the construction of another embodiment of the optical measuring apparatus of the present invention. In this optical measuring apparatus, an infrared light beam emitted from a halogen lamp 22 is collected by a lens 23 and made incident on an optical fiber 24. The optical fiber 24 separates the incident infrared light into light paths 25, 28 of the measure optical system and a light path 26 of the reference optical system. In the gap between light paths 25 and 28 of the measure optical system, a measured object (human finger 27) is inserted object during transmitted light measurement, while a douser is inserted to block the infrared light that passes from light path 25 to light path 28 during compensation light measurement. Light path 28 joins light path 26 of the reference optical system. The infrared beam emitted from optical fiber 24 is made incident on a photo diode 33 of the Ge type through a lens 29, a rotating disk 31 driven by the motor M, and a lens 32. As shown in FIG. 7, the rotating disk 31 is equipped with windows formed around its center of rotation, with inference filters 31a, 31c that transmit infrared light of a compensation wavelength domain and interference filters 31b, 31d that transmit the infrared light of a measure wavelength domain. A filter currently selected from interference filters 31a through 31d by rotating disk 31 can be detected by a photo sensor that detects a slit formed on a peripheral part of rotating disk 31. The photo sensor and the slit are not illustrated in the figures.

The output of photo diode 33 of the Ge type is input to the electric circuit composed of the amplifier 16, A/D converter 17, microcomputer 18, memory 19, and display 21 of the apparatus of FIG. 4 described in the second embodiment. A selected-filter signal that indicates which of the interference filters 31a to 31d is currently selected is input from photodiode 33 of the Ge type to the microcomputer 18. The microcomputer 18 determines absorbances by the same operations for the apparatus of FIG. 4 based on the output measurements of photodiode 33 and the selected-filter signal to determine the component concentrations of human body fluids.

In the construction of the third embodiment, the construction of the measure optical system and the reference optical system is simple by using an optical fiber, so that compact low-cost apparatus can be obtained.

Fourth Embodiment

Figure 8:
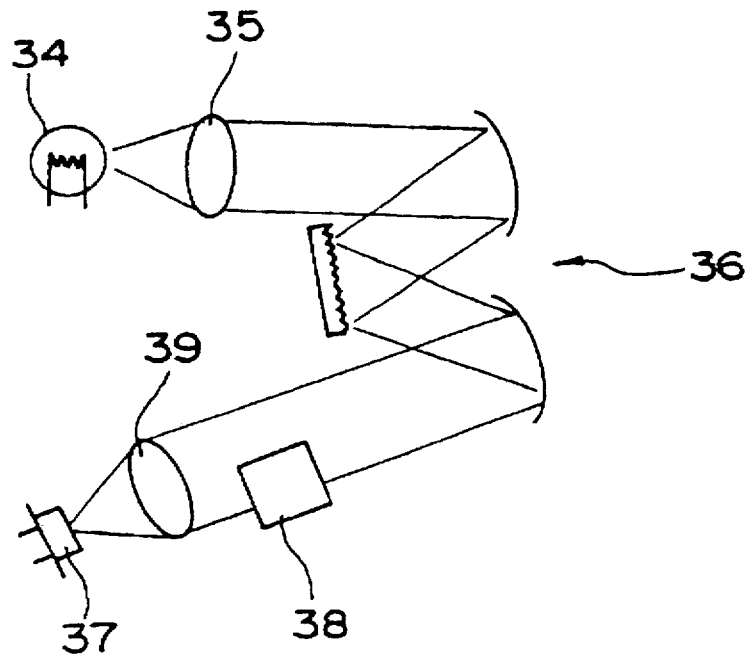
FIG. 8 shows a block diagram of another embodiment of optical measuring apparatus in accordance with the present invention.

FIG. 8 shows the construction of another embodiment of the optical measuring apparatus of the present invention.

This optical measuring apparatus is for measuring the component concentrations of resin materials. In this optical measuring apparatus, a beam of light emitted from a tungsten lamp 34 is made incident on a monochromator 36 of the diffraction grating type through a lens 35, and split thereby into the measure light of a measure wavelength domain and the compensation light of a compensation wavelength domain. Part of the light beam emitted from monochromator 36 of the diffraction grating type is directed to an optical cell 38, in which a liquid resin material is flowing, and the passing light is blocked by a douser when reference light is registered. The part of the light beam emitted from monochromator 36 of the diffraction grating type is incident on a lens 39 together with the other part of the light beam that has not been directed to optical cell 38, after passing through the resin material. The rejoined light is collectively input to a TGS infrared detector 37.

The output of the TGS infrared detector 37 is input to the electric circuit described in the second embodiment and shown in FIG. 4, including of the amplifier 16, A/D converter 17, microcomputer 18, memory 19, and display 21. A signal indicating which of the measure wavelengths and compensation wavelengths is currently selected is provided to microcomputer 18 by monochromator 36 of the diffraction grating type. The microcomputer 18 determines absorbances by the same operations as the apparatus of FIG. 4 to determine the component concentrations of the liquid resin material.

In the construction of the present fourth embodiment, a liquid resin material that flows in optical cell 38 can be continually measured in real time.

Fifth Embodiment

Figure 9:
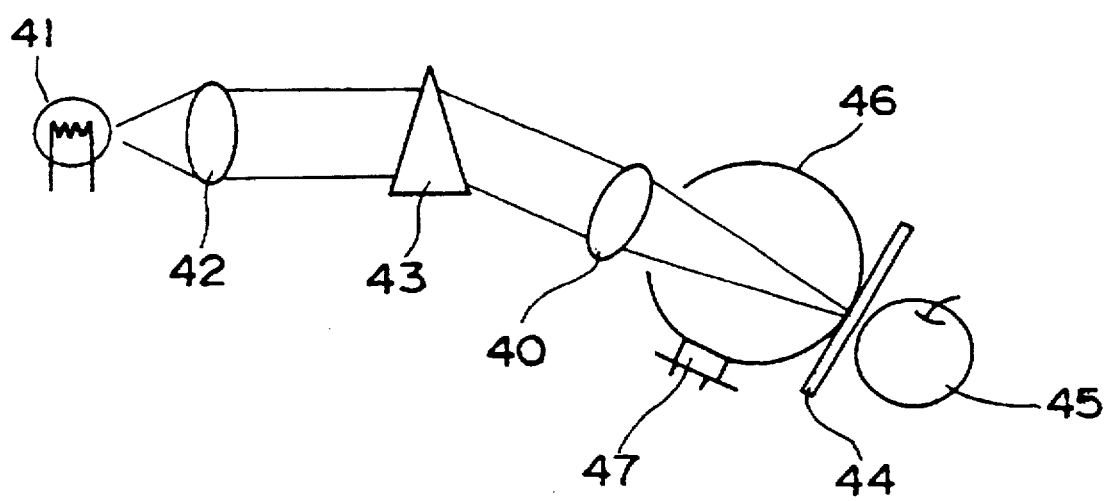
FIG. 9 shows a block diagram of another embodiment of optical measuring apparatus in accordance with the present invention.

FIG. 9 shows the construction of another embodiment of the optical measuring apparatus of present invention. This optical measuring apparatus is for measuring the sugar concentration of a fruit 45. In the optical measuring apparatus, a beam of light emitted from a halogen lamp 41 is made incident on a monochromator 43 of the prism type through a lens 42, and split thereby into the measure light of a measure wavelength domain and the compensation light of a compensation wavelength domain. The light beam emitted from monochromator 43 of the prism type is concentrated by a lens 40 and projected onto the fruit 45 through a silica plate 44. The light diffuse-reflected by fruit 45 is collected by an integrating sphere 46 and detected by a detector 47. The measured object, the fruit 45 is removed during the registration of reference light.

The output of detector 47 is input to the electric circuit including the amplifier 16, A/D converter 17, microcomputer 18, memory 19, and display 21 of the apparatus of FIG. 4 described in the second embodiment. A signal indicating which of the measure wavelengths and compensation wavelengths is currently selected is provided to microcomputer 18 by monochromator 43 of the prism type. The microcomputer 18 determines diffuse reflectances based on the signal and the output measurements of detector 47 by the same operations for the apparatus of FIG. 4 to determine the sugar concentration of the fruit 45.

In the construction of the fifth embodiment, the sugar concentration of the fruit 45 can be determined without damaging or destroying the fruit.

Sixth Embodiment

Figure 10:
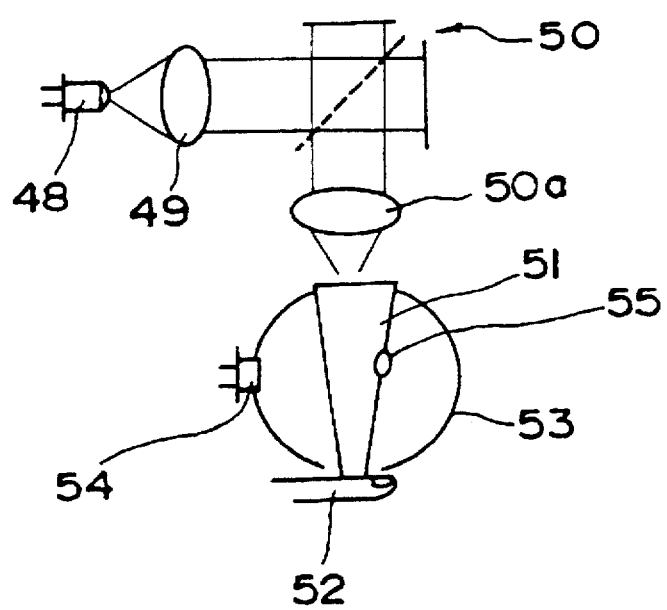
FIG. 10 shows a block diagram of another embodiment of optical measuring apparatus in accordance with the present invention.

FIG. 10 shows the construction of another embodiment of the optical measuring apparatus of present invention. This optical measuring apparatus is for measuring the component concentrations of human body fluids. In the optical measuring apparatus, a beam of light emitted from a light emitting diode 48 is made incident, through a lens 49, on an interference optical system 50 of the Fourier transform type, which splits the infrared light beam into the measure light of a measure wavelength domain and the compensation light of a compensation wavelength domain. The light beam emitted from interference optical system 50 of the Fourier transform type is concentrated by a lens 50a and made incident on a light cone 51. A human finger 52 is positioned at the opening tip of light cone 51 during the measurement of the component concentrations of human body fluids. The light cone 51 has an optical opening 55 at its side and is arranged inside an integrating sphere 53. Part of the light beam incident on light cone 51 is not projected onto finger 52, and collected by integrating sphere 53 through optical opening 55 together with the light passing through finger 52. The light collected by integrating sphere 53 is detected by a detector 54. The opening tip of light cone 51 is blocked by a douser during the registration of reference light.

The output of detector 52 is input to the electric circuit including the amplifier 16, A/D converter 17, microcomputer 18, memory 19, and display 21 of the apparatus of FIG. 4 described in the second embodiment. A signal indicating which of the measure wavelengths and compensation wavelengths is currently selected is provided to microcomputer 18 by interference optical system 50 of the Fourier transform type. Microcomputer 18 determines absorbances by finger 52 based on the signal and the output measurements of detector 54 by the same operations as the apparatus of FIG. 4 to determine the component concentrations of human body fluids.

In the construction of the sixth embodiment, light cone 51 is arranged inside integrating sphere 53, so that the constructions of the measure optical system and the reference optical system can be made simple and compact.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. An optical measuring method that irradiates a measured object with light from a light source and measures a spectrum of light transmitted through or reflected by the measured object, wherein the light source generates measuring light of wavelengths including wavelengths in a compensation wavelength domain at which the measured object almost completely absorbs the measuring light, said method comprising the steps of:

measuring the spectrum of the light generated by the light source;

irradiating the measured object with the light from the light source and measuring the spectrum of the light transmitted through or reflected by the measured object;

calculating a ratio of an intensity of the light transmitted through or reflected by the measured object to an intensity of the light generated by the light source in the compensation wavelength domain;

multiplying the intensity of the light generated by the light source at each wavelength by the ratio to obtain an informationless spectrum; and obtaining, as a compensated sample spectrum, a first difference spectrum by subtracting the informationless spectrum from the spectrum of the light transmitted through or reflected by the measured object.

2. The optical measuring method of claim 1 wherein a second difference spectrum is obtained, as a compensated source spectrum, by subtracting the informationless spectrum from the spectrum of the light generated by the light source and an absorbance spectrum is obtained from the compensated sample spectrum and the compensated source spectrum;

wherein a characteristic value of the measured object is determined based on the absorbance spectrum.

3. The optical measuring method of claim 1 wherein a temporary absorbance spectrum is obtained from the compensated sample spectrum and the spectrum of the light generated by the light source and an absorbance spectrum is obtained by compensating the temporary absorbance spectrum for additive errors by baseline compensation or differentiation;

wherein a characteristic value of the measured object is determined based on the absorbance spectrum.

4. The optical measuring method of claims 1, 2, or 3 wherein a standard material is added to the measured object so that transmittances in the compensation wavelength domain are approximately zero.

5. The optical measuring method of claim 4 wherein the standard material is water.

6. The optical measuring method of claim 5, wherein the compensation wavelength domain includes an absorption wavelength domain for O-H.

7. The optical measuring method of claim 4 wherein the compensation wavelength domain includes an absorption wavelength domain for C-H.

8. The optical measuring method of claim 1, wherein the measured object is one of a human body part, a resin material and a fruit.

9. The optical measuring method of claim 1, wherein the light source is one of a nichrome lamp, halogen lamp, tungsten lamp, and light emitting diode.

10. An optical measuring apparatus that irradiates a measured object with light to measure intensities of the light transmitted through or reflected by the measured object and measures a material value of the measured object based on the intensities, said optical measuring apparatus comprising:

a light source that generates measuring light of a measure wavelength domain for measuring a characteristic value of the measured object and of a compensation wavelength domain where light is almost completely absorbed by the measured object;

a spectroscopic optical system that splits the measuring light into the measure wavelength domain and the compensation wavelength domain;

a light path optical system that directs the measuring light emitted from said light source to a first light path and a second light path, where the measured object is in the second light path, said light oath optical system rejoining the first light path and the second light path;

a photometric unit that measures light emitted from said light path optical system to detect intensities of the light split into the measure wavelength domain and the compensation wavelength domain;

a memory that stores light intensities of the measure wavelength domain and the compensation wavelength domain output from said photometric unit during a reference measurement when a light-blocking material is arranged in, or the measured object is removed from, the second light path; and an arithmetic unit that calculates a ratio of a light intensity in the compensation wavelength domain detected by said photometric unit during ordinary measurement when the measured object is arranged in said the second light path to a light intensity in the compensation wavelength domain stored in said memory, obtains absorbances by arithmetically processing the ratio of the light intensity, light intensities stored in said memory, and output values of said photometric unit during the ordinary measurement, and determines the characteristic value of the measured object based on the absorbances.

11. The optical measuring apparatus of claim 10 wherein said arithmetic unit performs the computation $-\log\{(I_m - n \times I_o)/(n \times I_o)\}$ for light intensities $I_o$ stored in said memory and output values $I_m$ of said photometric unit during the ordinary measurement, where n is the ratio of the light intensity.

12. The optical measuring apparatus of claims 10 or 11 wherein said light path optical system includes an optical fiber, which has a first section that forms the first optical path and a second section that forms the second optical path, and the second section includes a measuring part where the measured object is arranged.

13. The optical measuring apparatus of claims 10 or 11 wherein said light path optical system includes an integrating sphere, on which said photometric unit is arranged.

14. The optical measuring apparatus of claims 10 or 11 wherein said light path optical system includes an integrating sphere and a light cone arranged inside said integrating sphere and having an optical opening that opens inside said integrating sphere.

15. The optical measuring apparatus of claims 10 or 11 wherein said spectroscopic optical system includes a Fourier transform interference optical system.

16. The optical measuring apparatus of claims 10, 11, or 12 wherein said spectroscopic optical system includes a rotating disk including filters some of which transmit the light of the measure wavelength domain and others of which transmit the light of the compensation wavelength domain that is almost completely absorbed by the measured object.

17. The optical measuring apparatus of claims 10 or 11 wherein said spectroscopic optical system includes a diffraction grating monochromator.

18. The optical measuring apparatus of claims 10 or 11 wherein said spectroscopic optical system includes a prism monochromator.

19. The optical measuring apparatus of claim 10, wherein the measured object is one of a human body part, a resin material and a fruit.

20. The optical measuring apparatus of claim 10, wherein said light source is one of a nichrome lamp, halogen lamp, tungsten lamp, and light emitting diode.

* * * * *